United States Patent [19]

Gurewich

[11] Patent Number: 5,759,542
[45] Date of Patent: Jun. 2, 1998

[54] COMPOSITIONS AND METHODS FOR THE DELIVERY OF DRUGS BY PLATELETS FOR THE TREATMENT OF CARDIOVASCULAR AND OTHER DISEASES

[75] Inventor: Victor Gurewich, Cambridge, Mass.

[73] Assignee: New England Deaconess Hospital Corporation, Boston, Mass.

[21] Appl. No.: 286,748

[22] Filed: Aug. 5, 1994

[51] Int. Cl.⁶ .................. A61K 38/49; C12N 9/72
[52] U.S. Cl. .................. 424/94.64; 435/215; 435/212
[58] Field of Search .................. 424/94.63, 94.64; 435/215; 530/311, 300

[56] References Cited

U.S. PATENT DOCUMENTS

5,023,078  6/1991  Halluin .................. 424/94.64
5,112,755  5/1992  Heyneker .................. 435/215

FOREIGN PATENT DOCUMENTS

0 395 918 A2  11/1990  European Pat. Off.

OTHER PUBLICATIONS

Lu, H. et al. *FEBS Letters* 356:56–59 (1994).
Bode et al., *The Journal of Biological Chemistry*, 262:10819–10823, (1987).
Bode et al., *Circulation*, 84:805–813 (1991).
Gurewich et al., *Federation of European Biochemical Societies*, 318:317–321 (1993).
Loza et al., *Thrombosis and Haemostasis*, 3:347–352 (1994).
Park et al., *Blood*, 73:1421–1425 (1989).
Rao, et al., *Thrombosis Research* 62:319–334 (1991).
Roberts, *The American Journal of Cardiology*, 67:1A–2A (1991).
Vaughan, et al., *Fibrinolysis*, 4:141–146 (1990).
Vaughn, et al. *The Journal of Biological Chemistry*, 264:264:15869–15874, (1989).

*Primary Examiner*—Karen C. Carlson
*Attorney, Agent, or Firm*—Fish & Richardson P.C.

[57] ABSTRACT

A fusion drug including an isolated portion of the A-chain of a urokinase-type plasminogen activator linked to a drug, wherein the A-chain portion binds stably to an outer membrane of a platelet. The $T_{1/2}$ of the fusion drug in plasma is thereby increased to about 4 to 5 days, and the fusion drug is automatically targeted to forming thrombi and sites of vascular injury. The fusion drug can thus be used to treat cardiovascular diseases, e.g., as adjunctive therapy to inhibit reocclusions in a patient after thrombolytic therapy or angioplasty.

11 Claims, 6 Drawing Sheets

COMPOSITIONS AND METHODS FOR THE DELIVERY OF DRUGS BY PLATELETS FOR THE TREATMENT OF CARDIOVASCULAR AND OTHER DISEASES

BACKGROUND OF THE INVENTION

The invention relates to the treatment and prevention of cardiovascular and other diseases.

Cardiovascular diseases include various forms of arteriosclerosis, thrombosis, embolisms, and transient arterial insufficiency, and have been treated by various methods. These diseases are all believed to involve platelets in their pathogenesis. Other vascular diseases which involve platelets include thrombotic thrombocytopenic purpura (Moskowitz's disease) and restenosis following thrombolytic or angioplasty therapy. The latter presents a particularly common and challenging problem.

For example, thrombolytic therapy, e.g., with streptokinase (SK) or tissue-type plasminogen activator (tPA), is widely used to dissolve potentially life-threatening blood clots that occur, e.g., after acute myocardial infarction. Angioplasty, e.g., percutaneous transluminal coronary angioplasty (PTCA), is used to open coronary artery stenoses. However, both thrombolytic therapies and angioplasty are associated with an undesirably high rate of reocclusion, and often reinfarction, which can occur within hours after successful lysis, and substantially attenuate the therapeutic effect. For example, reocclusions occur in about 29% of patients treated with tPA, Morrie et al., Am Heart, 122:375–380 (1991), Kalbfleisch, et al., Am. J. Cardiol., 69:1120–1127 (1992), and in about 10% of patients treated with SK, Yusuf et al., J.A.M.A., 260:2088-20-93 (1988). In addition, about 30% of stenoses opened by PTCA reocclude within three months.

Studies have demonstrated that such restenosis is characterized by neointimal hyperplasia due to smooth muscle cell (SMC) proliferation and to the synthesis of extracellular matrix. In addition, Agel et al., J. Pathol., 146:197 (1985), suggests that growth factors are involved in the etiology of atherosclerosis. For example, the SMC hyperplasia that accompanies atherosclerosis has been attributed to platelet-derived growth factor (PDGF), a potent SMC mitogen.

To counteract such undesirable reocclusions, various adjunctive therapies have been developed for use after thrombolysis. For example, aspirin, heparin, hirudin, thrombin inhibitors, platelet inhibitors, monoclonal antibodies to platelet glycoprotein IIb/IIIa, and activated protein C have all been identified as potential agents for use in such adjunctive therapies. In addition, β-blockers, calcium antagonists, angiotensin-converting enzyme inhibitors, and nitrates have been studied as potential adjuncts to thrombolytic therapy.

For example, a number of direct inhibitors of thrombin have been shown to be effective in preventing platelet-dependent arterial thrombosis and rethrombosis after thrombolytic reperfusion in animals. See, e.g., Haskel, Circulation, 83:1048–1056 (1991), Jang et al., Circ. Res., 67:1552–1561 (1990), Heras et al., Circulation, 82:1476–1484 (1990), Kelly et al., Blood, 77:1006–1012 (1991), and Sitko et al., Circulation, 85:805–815 (1992). One of these thrombin antagonists is hirudin, an anticoagulant derived from the leech, Hirudo medicinalis, Dodt et al., FEBS, 165:180–184 (1984).

Somatostatin, a naturally occurring tetradecapeptide, is known to inhibit certain growth factors, but has a short half-life in the blood stream. Therefore, a number of longer-acting analogs have been synthesized that have somewhat longer plasma half-lives. One such compound, the octapeptide angiopeptin, inhibits accelerated atherosclerosis in rabbit cardiac allografts, Foegh et al., Atherosclerosis, 78:229–36 (1989), and myointimal thickening in the rat following carotid artery desiccation injury, Lundergan et al., Atherosclerosis, 80:49–55 (1989); Lundergan et al., J. Am. Cell. Cardiol., 17:1328–1368 (1991).

In spite of their widespread use, adjunctive agents such as high dose heparin, and anti-thrombin or antiplatelet agents, can be associated with hemorrhagic complications such as systemic bleeding. These adjunctive therapies are also expensive and complicate thrombolytic therapy. Further, heparin has been shown to be of only limited efficacy in antagonizing the action of thrombin, and the various anti-thrombin and anti-growth factor agents, even the longer-lived somatostatin analogs, have relatively short half-lives once administered to a patient.

SUMMARY OF THE INVENTION

Applicant has discovered that a portion of the A-chain domain of urokinase-type plasminogen activators (u-PA), e.g., pro-urokinase (pro-UK) or high molecular weight urokinase (HMW-UK), is stably bound to the outer membrane of mammalian blood platelets, and that this portion of the A-chain can be linked to any one of a variety of drugs, e.g., cardiovascular drugs, to form a fusion drug in the form of a protein or polypeptide. These fusion drugs are automatically incorporated into the platelet membranes when administered to a patient and are thereby targeted to the site of platelet-mediated forming thrombi or vascular injury.

In contrast to pro-UK and other fibrinolytic and/or anti-thrombotic drugs, the novel fusion drugs bound to platelets also remain in the bloodstream for as long as the platelets remain in the circulation ($T_{1/2}$~4 to 5 days or longer), rather than being quickly cleared from the circulation within several minutes or hours.

Based on this discovery, the invention features novel fusion drugs, i.e., proteins or peptides, that include an isolated portion of the A-chain of a urokinase-type plasminogen activator linked to a drug, wherein the A-chain portion binds stably to an outer membrane of a platelet. The A-chain portion preferably includes amino acids 1 to 132 of the A-chain of pro-urokinase, or the sequence of amino acids of the A-chain portion is the sequence of amino acids 1 to 132 in SEQ ID NO:18.

The components of the fusion drug are linked, e.g., with a covalent bond, such as a disulfide bond. In another embodiment, the fusion drug is produced recombinantly, and the two components of the fusion drug are linked by a peptide bond.

The A-chain portion can also include a linker region from the C-terminus of the A-chain of the urokinase-type plasminogen activator, e.g., amino acids 133 to 158 of the A-chain of pro-urokinase.

The fusion drug can include a sequence of amino acids that provides a cleavage site for thrombin, the sequence including amino acids corresponding to amino acids 156 and 157 of pro-urokinase, or can further include a portion of the N-terminus of the B-chain of a urokinase-type plasminogen activator, such that the fusion drug includes a sequence of amino acids that provide a cleavage site for plasmin, the sequence including amino acids corresponding to amino acids 158 and 159 of pro-urokinase. Both thrombin and plasmin are generated locally at sites of intravascular thrombosis or injury and will cause local release of the cardiovascular drug portion of the fusion drug from the platelet surface. For example, the B-chain portion can include amino acids corresponding to amino acids 159 to 160 or 170 of pro-urokinase.

The drug portion of the fusion drug can be effective against a cardiovascular disease, can be a thrombolytic agent such as hirudin or a hirudin analog, or can be a growth factor antagonist such as somatostatin or a somatostatin analog.

The invention also features a fusion drug-platelet complex including a fusion drug stably bound to the outer membrane of a platelet.

In addition, the invention features a method of making a fusion drug by isolating a portion of the A-chain of a urokinase-type plasminogen activator, wherein the A-chain portion binds stably to an outer membrane of platelets, purifying a drug, and linking the A-chain portion to the drug. Alternatively, the fusion drug can be prepared by obtaining a first isolated nucleic acid encoding a portion of the A-chain of a urokinase-type plasminogen activator, wherein the A-chain portion binds stably to an outer membrane of platelets, obtaining a second isolated nucleic acid encoding a drug, inserting the first and second nucleic acids into an expression vector, wherein the first and second nucleic acids are operably linked in the expression vector, introducing the expression vector into a host cell, and culturing the host cell to allow the cell to produce the fusion drug.

The invention also features a general method of targeting a drug to a site of platelet-mediated forming thrombi and vascular injury in a patient by administering a fusion drug to the patient, thereby automatically targeting the drug to a site of platelet-mediated forming thrombi and vascular injury. A specific use for such targeting is featured in methods of treatment of a cardiovascular disease in a patient by administering to the patient an effective amount of a fusion drug, or by removing platelets from the patient, contacting the platelets with a fusion drug for a time sufficient to allow the fusion drug to bind to outer membranes of the platelets, and administering an effective amount of the resulting fusion drug-platelet complex to the patient.

This second method is less practical, but has the advantage of allowing a greater concentration of the drug to accumulate in the platelets, because it eliminates any effect of in vivo plasma clearance of the fusion drug prior to incorporation into the platelet membranes.

In addition, the invention features a method of adjunctive therapy to inhibit reocclusion in a patient after thrombolytic treatment by administering to the patient a fusion drug after the completion of the thrombolytic treatment and once every 1 to 10 days thereafter for the period of risk of reocclusion. The invention also provides a method of treating transient arterial insufficiency in a patient by administering a bolus of a fusion drug of claim 1 to the patient in an amount that inhibits the formation of occlusive thrombi, the amount of fusion drug is administered daily during periods of arterial insufficiency, and once every 1 to 3 days thereafter until the arterial insufficiency has stabilized.

As used herein, the term "A-chain" refers to the native A-chain of urokinase-type plasminogen activators such as pro-UK and HMW-UK (e.g., amino acids 1 to 158 of the full sequence of pro-UK as shown in SEQ ID NO:1 and FIG. 2), and variations in length or amino acid sequence of the native full-length A-chain, that have the ability to stably bind to the outer membrane of platelets. This stable binding to the outer membrane can be determined by the assay described below.

As used herein, the terms "stably bound" or "binds stably" when referring to a portion of the A-chain and the platelet outer membrane means that the A-chain portion does not dissociate from the platelet membrane after acid washing and/or sonic disruption of the platelets.

As used herein, the term "drug" includes active fragments or analogs of a drug, e.g., a protein or polypeptide, that have at least 50% of the activity of the full-sized drug. For example, if the drug is hirudin, an active fragment or analog of hirudin has at least 50% of the thrombin inhibitory activity of native hirudin (e.g., as measured in a standard S-2238 chromogenic assay). If the drug is somatostatin, an active fragment or analog of somatostatin has at least 50% of the inhibitory activity of native somatostatin (e.g., as measured in assays of inhibition of smooth muscle cell proliferation as described in Ramwell et al., U.S. Patent No. 5,147,856).

A drug can be a protein, peptide, or polypeptide, and can be proteolytically cleaved from a native protein, recombinantly expressed, or synthesized by methods known to those skilled in the art. Drugs can be made of D- or L-amino acids or a mixture of both. Drugs with a D-amino acid as the amino- or carboxyl-terminal amino acid are particularly preferred, in order to inhibit proteolytic degradation of the fusion protein.

Chemical derivatives of the above drug proteins, peptides, or polypeptides are also within the invention. Chemical derivatives are defined as polypeptides to which one or more negatively charged side groups have been added. Derivatization methods, which are well known in the art, include, but are not limited to sulfation, methyl sulfonation, phosphonation and carbonation of the tyrosine hydroxyl group, or sulfonation, phosphonation and carbonation of the tyrosine benzoyl meta carbon.

Either or both termini of the fusion protein can be protected from proteolytic degradation by the presence of a standard protective group such as an aldehyde. Aminoterminal blocking groups such as t-butyloxycarbonyl, acetyl, succinyl, methoxysuccinyl, suberyl, adipyl, azelayl, dansyl, benzyloxycarbonyl, fluorenylmethoxy-carbonyl, methoxyazelayl, methoxyadipyl, methoxysuberyl, and 2,4,-dinitrophenyl are also useful.

As used herein, the term "operably linked" means that the nucleic acids encoding the portion of the A-chain and the drug are inserted into an expression vector such that the A-chain portion is linked to the N-terminus of the amino acid sequence of the drug in the resulting fusion drug produced by the host cell containing the expression vector.

The period of high risk of reocclusion after thrombolytic treatment is typically about 3 to 6 months. In the first 48 hours after treatment, the risk is between 5 and 30 percent. From 48 hours to three months, the risk is an additional 30 percent, i.e., a vessel that is open after 48 hours still has a 30% chance of reocclusion within the next three months. From 3 to 6 months, the risk is an additional 40 percent.

In additional embodiments, the invention features a nucleic acid encoding a fusion drug, and a host cell containing a nucleic acid encoding a fusion drug.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

Figure 1:
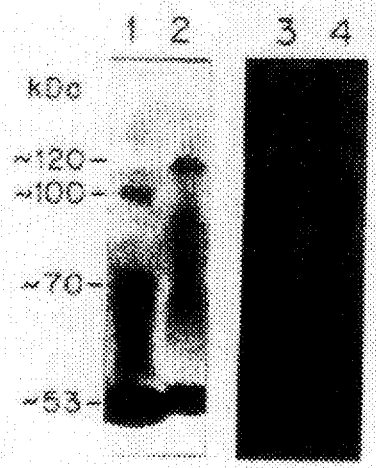
FIG. 1 is a zymogram of washed platelets and platelet-poor plasma with added pro-UK, with and without acid washing.

Applicant's findings suggest that a portion or domain of the A-chain of high molecular weight u-PA, e.g., pro-UK, is incorporated or intercalated into the lipid portion of the outer membrane of platelets. This portion can be linked to a protein or polypeptide effective against vascular or intravascular disease to form a fusion drug or conjugate. When this fusion drug is administered to a patient it becomes stably bound to the patient's platelets to gain an exceptionally long duration of action which cannot be approximated by any other known method.

Moreover, the effect of the fusion drug, e.g., an antithrombotic action, is greatly enhanced compared to that of the conventional form of the drug in plasma, because this platelet-bound form of the fusion drug is targeted at the site of platelet concentration directly in forming blood clots or sites of vascular injury, which provides a more localized and specific effect.

This stable binding of the A-chain of u-PA to the platelet membrane is specific, in that it occurs with pro-UK and high molecular weight (~50–53 kDa) two-chain UK (HMW-UK), but does not occur with tPA, SK, or low molecular weight UK (LIMW-UK), which indicates that incorporation is indeed mediated by a domain of the A-chain of u-PA. This incorporation does not require carbohydrate side-chains, since non-glycosylated UK is similarly incorporated.

Applicant discovered this characteristic of the A-chain of u-PA by studying the incorporation of pro-UK into platelets as described below. The A-chain of pro-UK anchors the catalytic region of pro-UK to the platelet surface. This greatly extends pro-UK's fibrinolytic effect since natural, unincorporated pro-UK in plasma has a $T_{1/2}$ of only about 6 to 8 minutes. Moreover, since the platelet incorporation is very sensitive (nanogram quantities were shown to be picked up from whole blood) and highly selective, it allows pro-UK to be given subcutaneously, intramuscularly, or orally, instead of only intravenously. Such administration provides for a protracted and targeted fibrinolytic and/or antithrombotic effect suitable for self administration for the treatment or prevention of atherothrombotic disease.

EXPERIMENTAL STUDIES WITH PRO-UK

Applicant has conducted various in vitro and animal studies to determine the specificity, effective half-life, and anti-thrombotic effect of the newly discovered platelet membrane-bound u-PA. Native pro-UK purified from the culture medium of a human kidney tumor cell was obtained from Collaborative Research, Inc. (Bedford, Mass.). Recombinant pro-UK (rec-pro-UK) from $E.\ coli$ was obtained from Farmitalia Carlo Erba (Milan, Italy). LMW-UK was obtained from Abbott Laboratories (Chicago, Ill.).

Preparation of Platelets

Human platelets were prepared from venous blood added to 3.8% citrate (9:1). Platelet-rich plasma (PRP) was obtained by centrifuging this blood-citrate mixture at 160 g for 15 minutes at room temperature. Platelet-poor plasma (PPP) was obtained by adding prostaglandin $E_1$ ($PGE_1$) (1 µM) to the PRP, centrifuging this mixture at 725×g, and removing the PPP. The platelets were resuspended by gentle mixing in HEPES Tyrodes-albumin buffer (HTA) containing 128 nM NaCl, 8.9 mM $NaHCO_3$, 5.6 mM dextrose, 10 mM HEPES 0.35 mg/ml BSA, 12 mM KCl, 3 mM KCl, 3 mM $KH_2PO_4$, and 3 mM $MgCl_2$, with a pH of 7.5. The washing was repeated twice, and the supernatant removed after centrifugation each time. Platelet counts were determined in a Coulter counter (Coulter Electronics, Hialeah, Fla.).

Endoaenous U-PA in Platelets

FIG. 1 is a zymogram which shows the endogenous u-PA intrinsic to platelets and plasma. Lane 1 shows platelets ($1 \times 10^8$) washed once in HTA buffer with a dominant plasminogen activator band of activity at ~53 kDa corresponding to u-PA. In addition, a band at ~70 kDa corresponds to tPA, which has previously been shown to bind to platelets by a specific, low affinity binding site. Vaughan et al., $J.\ Biol.\ Chem.$, 264:15869-74 (1989). In addition, a ~100 kDa band was seen in the platelets, consistent with a UK:plasminogen activator inhibitor-1 (PAI-1) complex. Lane 2 shows the corresponding PPP, which also showed a band of u-PA activity, and a ~120 kDa band consistent with a tPA:PAI-1 complex. The UK:PAI-1 complex was invariably absent in the PPP (lane 2).

From the zymograms (not shown) of PPP (1–20 µl) and platelets ($10^7$–$10^8$), it was estimated the about 20% of the u-PA in blood was present in platelets based on their zymographic activities. The final wash (20 µl HTA buffer) was invariably devoid of activity, indicating that the buffer remaining with the platelet pellet was not the source of the zymographic activity.

Loading Platelets With U-PA, TPA, or Streptokinase

To determine whether the platelets incorporate pro-UK, UK, tPA, or streptokinase, washed platelets were incubated (37° C.) in PPP or HTA buffer ($4 \times 10^8$ platelets/ml), enriched with 0.5 µg/ml of native pro-UK or rec-pro-UK, HMW-UK, LMW-UK (which is missing most of the A chain), tPA, or streptokinase for 5 minutes. The two UK preparations, tPA, and streptokinase were incubated only in the buffer to avoid complexation with inhibitors naturally found in plasma. Thereafter, the platelets were recovered by centrifugation (725×g for 15 min.), washed twice in HTA buffer, resuspended in bank plasma, and reincubated for 0.5, 1, 2 and 22 hours. At the end of the final incubation period, the platelets were recovered by centrifugation, washed twice in HTA buffer and examined by zymography on plasminogen enriched casein plates. The corresponding PPP (20 µl) at the end of each incubation period was examined alongside the platelets. These tests showed that only high molecular weight pro-UK and UK, having a MW of about 53 kDa, is incorporated.

Thus, the incorporation of u-PA into the platelet membrane is specific for HMW (53 kDa) u-PA, either native glycosylated or recombinant unglycosylated, and either the single-chain proenzyme (pro-UK) or the two-chain enzyme (HMW-UK). No incorporation was found with LMW (33 kDa) u-PA (which lacks the A-chain), tissue plasminogen activator (tPA), or streptokinase. This confirms the finding that incorporation is dependent on the A-chain of u-PA, which bears the growth factor and kringle domains, amino acids 1 to 132 (shown in FIG. 2), and up to the endpoint of the A-chain, Lys$^{158}$, but not the catalytic site, amino acids 159 to 411 of u-PA. The two arrows in FIG. 2 indicate the plasmin cleavage (activation) site (Lys$^{158}$-Ile$^{159}$, arrow A) and the thrombin cleavage site (Arg$^{156}$-Phe$^{157}$, arrow B) in the primary amino acid sequence of single chain u-PA (proUK)(SEQ ID NO:18).

Acid Washing of Platelets

Platelets loaded with pro-UK were washed in acid (pH 3.0) to determine whether the pro-UK could be dissociated from the platelets. A pellet of ~1×10$^8$ washed platelets loaded with pro-UK as described above was resuspended in 1.0 ml of 20 mM citrate (pH 3.0), 0.15 M NaCl, and 0.3 mg/ml BSA. After 5 min, the platelets were spun down and resuspended in 10 ml of HTA buffer. After an additional 5 min., the platelet pellet was recovered by centrifugation and then analyzed by zymography. Acid washing by this procedure was shown to completely remove platelet-bound tPA and prekallikrein (which are bound to surface receptors on the platelet), but not platelet-bound pro-UK. This finding establishes that the platelet-bound pro-UK is not bound to a u-PA receptor on the platelet surface.

As shown in FIG. 1, when platelets preincubated with native pro-UK (0.5 µg/ml) in PPP for 5 min. were washed twice in HTA buffer, the tPA band seen in lane 2 is no longer seen in lane 3. The increased density of the bands in lanes 3 and 4 was due to additional pro-UK in the platelets as a result of the preincubation. Subsequent acid washing of the platelets induced only slight reduction in the intensity of the u-PA or u-PA:PAI-I complex, and did not significantly dissociate the pro-UK (lane 4).

Figure 3:
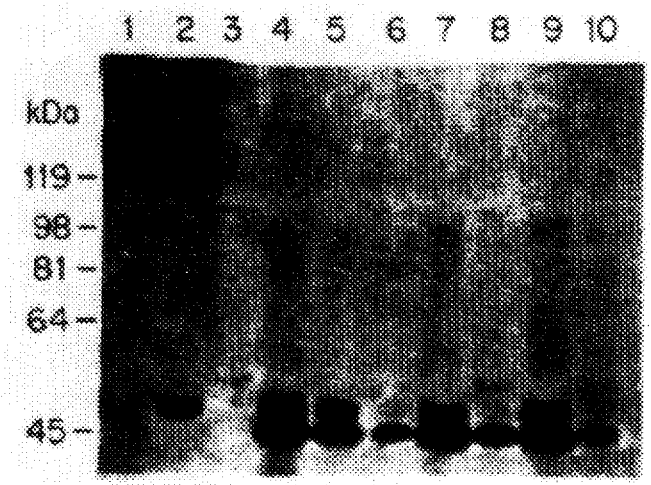
FIG. 3 is a zymogram of washed platelets and platelet-poor plasma incubated with recombinant pro-UK (recpro-UK).

As shown in FIG. 3, the uptake of pro-UK from the ambient fluid was most easily distinguished from endogenous pro-UK when rec-pro-UK was used, since it migrated ahead of the endogenous pro-UK. Rec-pro-UK is non-glycosylated, i.e., has no carbohydrate side-chains, and therefore has a lower molecular weight than endogenous pro-UK, which leads to its faster migration in SDS-PAGE gels. The control platelet preparation is shown in lane 2 alongside the control PPP in lane 3. The PPP induced no lysis bands due to the relatively short (14 hour) incubation time of the plate, since the amount of pro-UK in the PPP sample was less than in the platelets. The higher MW lysis zone from the endogenous pro-UK intrinsic to platelets was similar in all the lanes indicating no significant differences in the number of platelets in each sample, and that the endogenous pro-UK in platelets was not dissociated by the incubations in PPP for up to 22 hours. The platelets incubated with rec-pro-UK and then washed and reincubated in normal, unenriched PPP for 30 minutes (lane 4), 1 hour (lane 5), 2 hours (lane 7) and 22 hours (lane 9) induced comparable lysis zones, indicating no apparent dissociation of the rec-pro-UK over this time period. Lane 1 shows molecular weight markers.

FIG. 3 also shows a small but unchanging amount of rec-u-PA activity in the corresponding PPP at the end of each incubation period (lanes 6, 8, and 10) indicating that a fraction of the rec-pro-UK was released within the first 30 minutes, probably representing the unincorporated portion. However, the bulk of the intra-platelet rec-pro-UK remained unaffected by the incubation, regardless of the length of the incubation period, consistent with incorporation into the platelets. Moreover, this portion of the rec-pro-UK also resisted dissociation by acid washing as shown for native pro-UK in FIG. 1.

Incubation of platelets with native HMW-UK in HTA buffer induced similar uptake of the UK. By contrast, incubation with LMW-UK or tPA in HTA buffer at the same concentrations induced no uptake by platelets.

Both endogenous pro-UK intrinsic to platelets, and exogenous pro-UK, were incorporated by platelets, as evidenced by a resistance to dissociation by acid washing or by prolonged (22 h) incubation in a pro-UK-poor environment. Platelets contain an estimated 20% of the pro-UK present in the blood of healthy subjects.

Pro-UK is Incorporated Into Platelet Membranes

Pro-UK was labelled with 125I via a lactoperoxidase reaction using Enzymobeads (BioRad Laboratories, Richmond, Calif.) and incubated with platelets to determine whether the pro-UK was bound to the open canalicular system (OCS) of the platelet membrane. Autoradiography electron microscopy of these platelets gave identical images before and after osmotic swelling of the platelets in distilled water, which obliterates the OCS, indicating that the pro-UK was not merely bound to the surface canaliculae, but was incorporated or internalized into the platelet.

Platelets were then broken up by three 10 minute sonications followed by centrifugation at 10,000 g for 10 minutes. The platelet membranes were then separated from the supernatant by centrifugation at 100,000 g for about 10 minutes. All of the endogenous and the exogenous pro-UK was found by zymography to be firmly associated with the membrane, which indicated that the pro-UK was incorporated into the platelet membrane.

Incorporation of u-PA into the platelet membrane is dose dependent, not reversible by acid washing, and difficult to saturate, indicating that incorporation into the membrane is not mediated by any known receptor. Although a platelet-receptor for the 53 kDa u-PA has previously been reported by Vaughan et al., Fibrinolvsis, 4:141–146 (1990), this alleged receptor is not involved in the membrane uptake of u-PA described because incorporation was blocked by low pH or high salt, and these same buffer conditions failed to remove u-PA once it was incorporated into the platelet membrane. In fact, no method for removing the membrane-bound u-PA has been found. Furthermore, a 50 to 100-fold excess of unlabeled pro-UK did not inhibit incorporation of radiolabeled u-PA into platelets.

Figure 4A:
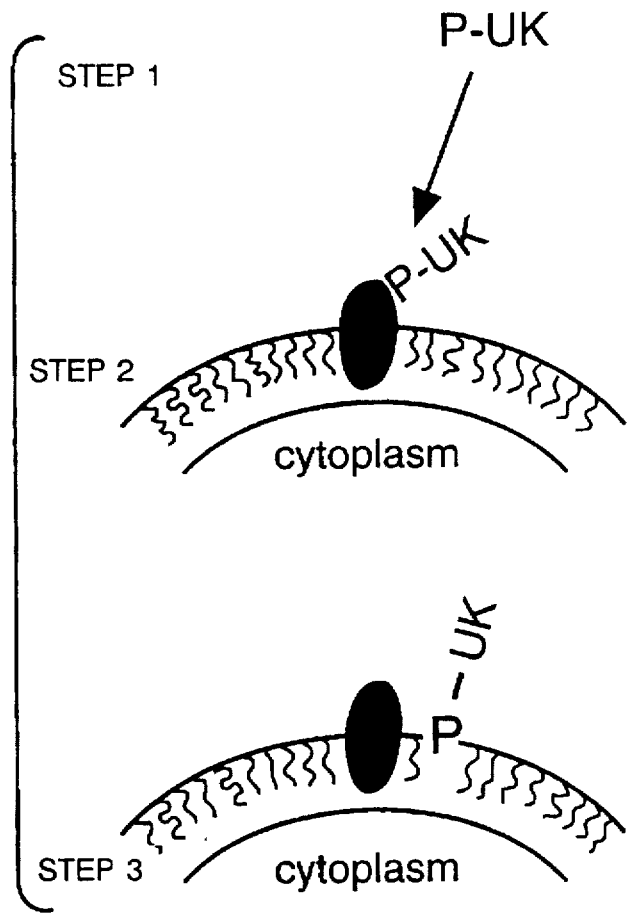
FIG. 4A is a schematic of the proposed two-step mechanism for u-PA incorporation into platelet membranes.

Based on these results, a two-step incorporation mechanism is postulated. In the first step, u-PA binds transiently with a platelet membrane protein yet to be identified in a high-affinity interaction that leads to a conformational change in the u-PA that exposes a hydrophobic region of the A-chain. In the second step, this hydrophobic region of the A-chain of u-PA is introduced into the plasma membrane lipid layer resulting in rapid intercalation of this A-chain region into the lipid layer of the membrane. At the same time, the catalytic domain on the u-PA B-chain remains outside of the platelet membrane, because the plasminogen activating activity and interaction with inhibitors (e.g., GGAck) of platelet membrane-bound u-PA is unimpaired. This pathway is illustrated schematically in FIG. 4A.

Figure 4B:
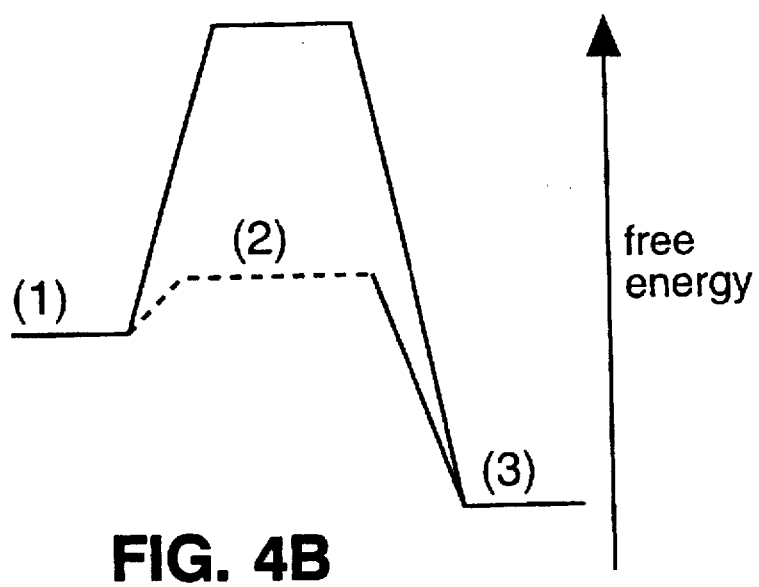
FIG. 4B is a graphical representation of the free energy of the mechanism of FIG. 4A.

The incorporation of u-PA into the platelet membrane is energy independent in that it is not inhibited by cold temperature (4° C.) or by a wide spectrum of metabolic or other inhibitors (cytochalasin B at 30 µg/ml, colchicine at 20 µM, procaine at 0.4%, dinitrophenol at 5 mM, sodium azide at 0.1%, sodium cyanide at 5 mM, EDTA at 5 mM, DMSO at 3.0%, $PGE_1$ at 1.0 AM). FIG. 4B graphically illustrates the direction of free energy in the pathway depicted in FIG. 4A.

Figure 5:
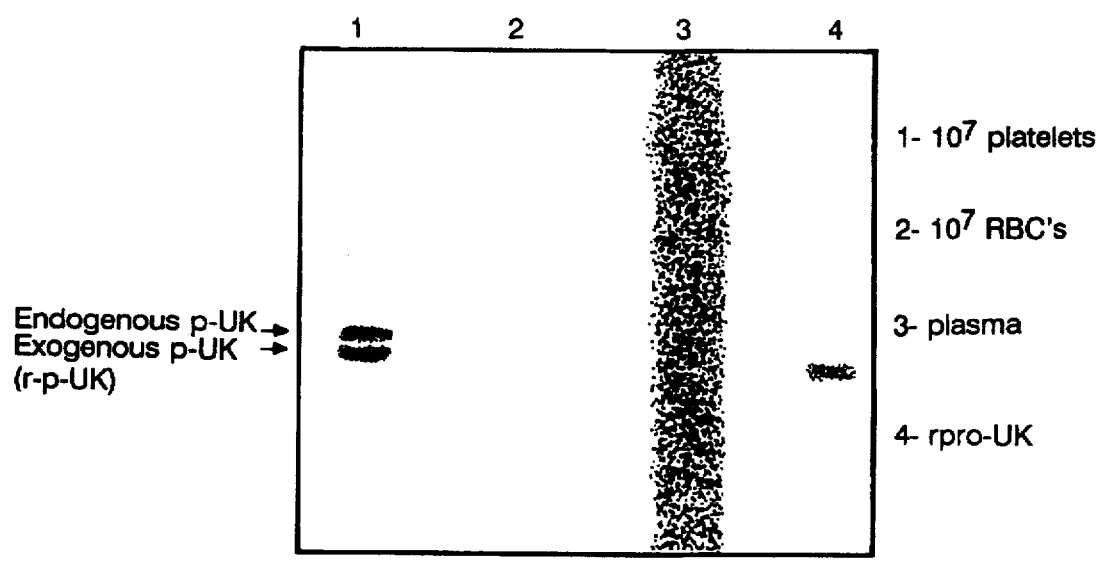
FIG. 5 is a zymogram showing endogenous and rec-pro-UK incorporated into platelets but not red blood cells from the same blood.

Furthermore, the phenomenon of membrane incorporation of u-PA is selective for platelets, since equivalent incorporation could not be demonstrated in human red cells, monocytes, or endothelial cells using the same incubation conditions described above. For example, this selectivity was demonstrated by experiments in which pro-UK was incubated in citrated whole blood followed by isolation of the red cells and platelets. Despite the 1,000-fold greater number and greater surface area of red blood cells, all the detectable pro-UK was found in the platelets. This is illustrated by the zymogram of FIG. 5, which shows endogenous and rec-pro-UK in the platelets, but not in the red cells from the same blood. Lane 1 shows $10^8$ platelets, lane 2 shows $10^8$ red blood cells, lane 3 shows plasma, and lane 4 shows rec-pro-UK.

Figure 6:
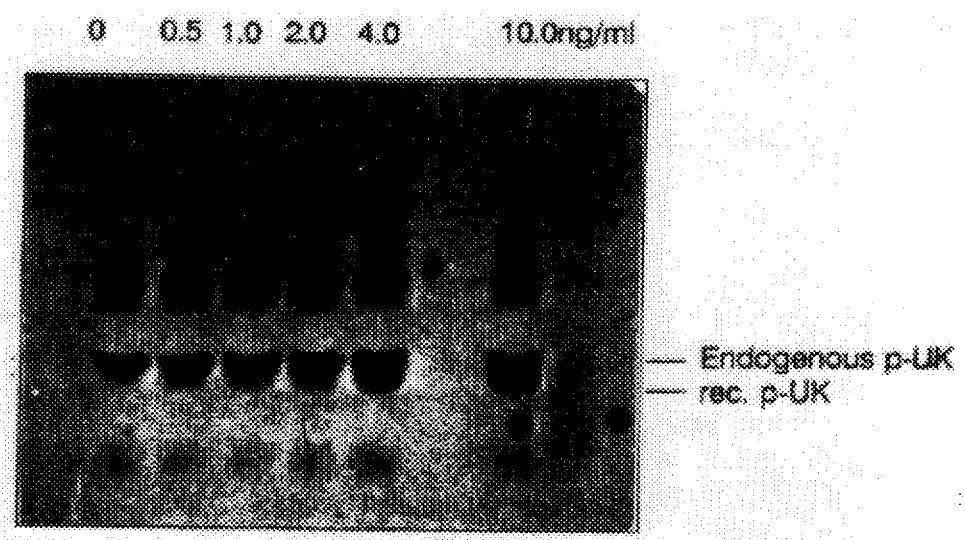
FIG. 6 is a zymogram showing platelets isolated from whole blood incubated for 30 minutes with 0 to 10 ng/ml rec-pro-UK.

Platelet uptake of pro-UK in whole blood also was found to be sensitive to very small concentrations of pro-UK. For example, when citrated whole blood was incubated with 0.5 to 10 ng/ml of rec-pro-UK for 30 minutes, zymographically detectable quantities were taken up at a concentration of $\geq 0.5$ ng/ml. Rec-pro-UK from *E. coli* was used in these experiments because it is non-glycosylated and therefore migrates ahead of the endogenous native pro-UK on SDS gel electrophoresis. At a concentration of about 4 ng/ml, about 20% of this amount was incorporated into the platelets, which is about the same percentage of endogenous pro-UK found in platelets in normal human blood. This is illustrated by the zymogram shown in FIG. 6, which shows platelets isolated from whole blood incubated for 30 minutes with 0, 0.5, 1.0, 2.0, 4.0, and 10 ng/ml rec-pro-UK (lanes 1 through 6, respectively).

Animal Studies

Human rec-pro-UK (0.5 mg/kg bolus) was administered i.v. over one minute into dogs and allowed to mix in the blood with dog platelets to determine whether human pro-UK is incorporated into these dog platelets. Blood samples were collected at 0 min., 15 min., 30 min., 1 hour, and 2 hours. The pro-UK in the platelets and plasma was analyzed by casein autography as described in Vassalli et al., *J. Exp. Med.*, 159:1653–1668 (1984), which is incorporated herein by reference. Considerable uptake of rec-pro-UK was seen in the dogs, and the amount of pro-UK shown to be incorporated in a sample taken at 15 minutes after injection of the pro-UK did not change over the two hour period of observation, i.e., there was about the same amount of pro-UK in the platelets in the 2 hour sample as in the 15 minute sample. No rec-pro-UK was detectable in the plasma samples after 30 minutes due to the rapid clearance of pro-UK from plasma.

Applicant has also discovered that under similar conditions, rabbit platelets do not incorporate human pro-UK. A 0.5 mg/kg bolus of pro-UK was injected intravenously into rabbits, and the plasma and platelets were tested at 0 min., 15 min., 30 min., and hourly thereafter for 5 hours. None of the human rec-pro-UK was incorporated into the rabbit platelets. Applicant also found that rabbit platelets do not appear to contain any endogenous rabbit pro-UK, whereas dog platelets contain substantial amounts of dog pro-UK.

Preparation of Fusion Drugs

The fusion drugs include a portion of the A-chain linked to a drug, e.g., a cardiovascular drug.

The A-Chain Portion

The A-chain portion in the fusion drug preferably includes the region of the u-PA molecule from the amino terminus through the kringle domain (amino acids 1 to 132) to ensure stable binding to, or incorporation into, platelet outer membranes. This portion of the A-chain of u-PA serves as a vehicle to attach the fusion drugs to the platelet outer membrane. In addition, a portion of a linker region between the kringle domain and the B-chain of pro-UK (amino acids 133 to 158) can be included in the fusion drug to allow separation of the A-chain and drug portions of the fusion drug.

The linker region has two functions. First, it provides a spacer between the A-chain domain which is incorporated into the platelet outer membrane and the drug which is outside the membrane. Second, it provides a mechanism by which the drug can be released locally from the platelet-bound fusion drug since the linker region provides a cleavage site for thrombin, which corresponds to the natural thrombin cleavage site between amino acids $Argl^{156}$ and $Phe^{157}$ in pro-UK.

The fusion drug can also be designed to include a portion of the B-chain, e.g., amino acids 159 to 170, between the A-chain portion and the drug to form a plasmin cleavage site which corresponds to the natural plasmin cleavage site between amino acids $Lys^{158}$ and $Ile^{159}$ in pro-UK.

The entire A-chain including the linker region, and the entire B-chain are encoded by the corresponding portions of the nucleic acid sequence of pro-UK (SEQ ID NO:1). The full nucleic acid sequence encoding pro-UK is also described in Verde et al., *P.N.A.S.. USA*, 81:4727-31 (1984). Recombinant pro-UK (SARUPLASE™) is available from Gruenental, Aachen Germany, or from Collaborative Research, Inc., Bedford, Mass. Further, the A-chain can be isolated by enzymatically cleaving two-chain UK with plasmin which cleaves at the $Lys^{135}$–$Lys^{136}$ site. Alternatively, the A-chain can be isolated by very gentle reduction of u-PA with dithiothreitol (DTT) which reduces the disulfide bond at the $Cys^{148}$–$Cys^{279}$ site, that links the A and B chains of UK or pro-UK. The B chain is then isolated from the mixture by affinity chromatography on Benzamidine SEPHAROSE®, leaving the A chain for use in chemical conjugation as described below. A portion of the A-chain of pro-UK useful to prepare the fusion drugs is also commercially available from American Diagnostica, Connecticut.

The following assay can be used to determine whether a particular portion of the A-chain binds stably to the outer membrane of platelets. First, the A-chain portion to be tested is labelled, e.g., with $^{125}$iodine, using standard techniques. Second, the labelled A-chain portion is added to a mixture of platelets in plasma and incubated for 15 minutes at a constant temperature, e.g., at room temperature. Third, the platelets are washed and centrifuged until all the unbound labelled A-chain portion is removed. Fourth, any labelled A-chain portion bound to the platelets is detected, e.g., with a gamma counter; label present on the platelets indicating that the A-chain portion binds to the platelets. If the labelled A-chain portion binds to the platelets, they are acid washed as described above and again analyzed for label to confirm that this A-chain portion in fact remains stably bound to the platelets.

The Drug Portion

The A-chain is linked to a drug, e.g., one effective against a cardiovascular disease. The drug portion of the fusion drug is preferably one whose efficacy can be greatly enhanced by this pathway, either through extension of its half-life or by improvement of targeting. Suitable drugs include heparin, antithrombins like hirudin, and inhibitors of growth factors, e.g., somatostatin or certain of its analogs.

Cardiovascular drugs, e.g., antithrombins and anticoagulants such as hirudin and related analogs, and growth factor antagonists, are used for their antithrombotic or antirestenosis effects. While effective, they typically have a short intravascular half-life and are untargeted. As with all anticoagulants, a systemic anticlotting state is induced which results in a bleeding diathesis. A fusion drug consisting of a cardiovascular drug, e.g., hirudin, and the A-chain of u-PA targets these agents to a developing thrombus or injured artery and greatly extends the half-life of these drugs.

Hirudin and Analogs

Recombinant hirudin having the sequence of the native protein, Dodt et al., FEBS 1104, 165:180–184 (1984) [r-Hirudin LU 52369, specific activity: 17,000 antithrombin units (ATU)/mg] can be obtained from Knoll AG, Ludwigshafen, Germany. Fragments and derivatives of hirudin with anti-thrombin and anti-coagulant activity useful in the present invention are known in the art. Examples include Hirudin PA (SEQ ID NO:2) described in Dodt et al., U.S. Pat. No. 4,767,742; a polypeptide described in Winant et al., U.S. Pat. No. 5,118,790, defined by the sequence X-AA$_3$-[AA$_4$-AA$_{62}$]-AA$_{63}$-Z, where X is hydrogen or an N-terminal extension sequence corresponding to some or all of the native hirudin sequence, AA$_3$ is a conservative amino acid residue other than tyrosine that is not susceptible to electrophilic chemical modification, AA$_4$-AA62 are amino acids 4 to 62 of the native hirudin, AA$_{63}$ is a tyrosine residue or a modified tyrosine residue that contains an electron-withdrawing substituent in the 3-, or 3-, 5-positions of the phenyl ring, and Z is a hydroxyl group or a C-terminal extension corresponding to some or all of the native hirudin sequence; and various hirudin peptidomimetic analogs ("hirulogs") and other hirudin analogs described in Maranganore, J.M., European Patent Application No. 333, 356, e.g., characterized by the sequence Asn-Gly-Asp-Phe-Glu-GluIle-Pro-Glu-Glu-Tyr-X (SEQ ID NO:3) and D-retro forms thereof, where X is COOH, Leu or Leu-Gln, or the sequence Y-Phe-Glu-Glu-Ile-Pro-Glu-Glu-Tyr-Z (SEQ ID NO:4) and D-retro forms thereof, where Y is NH$_2$ or an amino protecting group, and Z can be COOH, Leu, or Leu-Gln, and the tyrosine residue is characterized by the presence of a negatively charged side group.

Other Thrombin Inhibitors

Other thrombin inhibitors known in the art and useful in the present invention include antithrombin III, Sheffield et al., Blood, 79:2330–2339 (1992); β,β' monochlormethylene diadenosine 5'5'''-p$^1$p$^4$-tetraphosphate, Kim et al., P.N.A.S., USA, 89:11056–11058 (1992); short boroarginine peptides such as Ac-(D)Phe-Pro-boroArg-OH, Boc(D) Phe-Pro-boroArg-C$_{10}$H$_{16}$, H-(D) Phe-Pro-boroArg-OH, and H(D) Phe-Pro-boroArg-C$_{10}$H$_{16}$, Kettner et al., J. Biol. Chem., 265:18289–18297 (1990); synthetic peptides such as D-PhePro-Arg (CSAP), Asn-Gly-Asp-Phe-Glu-Glu-Ile-Pro-Glu-Glu-Tyr(OSO$_3$)-Leu (SEQ ID NO:5)(the sulfated C-terminal dodecapeptide of hirudin, ESAP), and D-Phe-Pro-Arg-Pro(Gly)$_4$-Asn-Gly-Asp-Phe-Glu-Glu-Ile-Pro-Glu-Glu-Tyr-Leu (SEQ ID NO:6)(BAP, Kelly et al., P.N.A.S., USA, 89:6040–6044, 1992); 3,4,-dihydro-3-benzyl-6-chloromethylcoumarin, Mor et al., Biochim. Biophys. Acta, 1038:119–124 (1990); D-phenylalanyl-prolyl-arginine chloromethyl ketone-treated α-thrombin (PPACK-IIa), Schmaier et al., Thromb. Res., 67:479–489 (1992); tripeptide inhibitors such as D-Phe-Pro-Arg-H (ALD) and D-Phe-Pro-Arg-CH$_2$Cl (CMK), Bagdy et al., Thromb. Res., 67:221–231 (1992); benzamidine-based inhibitors such as Nα-(β-naphthylsulfonylglycyl)-4-amidinophenylalanine piperidide (NAPAP), Sturzebecher et al., Biol. Chem. Hoppe-Seyler, 373:491–496 (1992); arginine-based inhibitors such as (2R,4R)-4-methyl-1-[N$^α$-(3-methyl-1,2,3,4-tetrahydro-8-quinolinesulphonyl)-L-arginyl]-2-piperidine carboxylic acid (MQPA), Bode et al., Eur. J. Biochem., 193:175–182 (1990); thrombin inhibitors incorporating a scissile peptide bond such as N$^α$-acetyl[D-Phe$^{45}$, ArgΨ (COCH$_2$)$^{47}$, Gly$^{48}$]desulfo hirudin$^{45-65}$ (P79), DiMaio et al., FEBS Lett., 282:47–52 (1991); and ketomethylene pseudopeptides such as [Ac-(D)-Phe$^{45}$, Pro$^{46}$, ArgΨ (COCH$_2$)CO$^{47,48}$,Gly$^{49}$] Hirudin$^{45-65}$ (Hirutonin-1), [Ac-(D)-Phe$^{45}$,Pro$^{46}$,ArgΨ[COCH$_2$]CH$_2$CO$^{47}$]Hirudin$^{45-65}$ (Hirutonin-2), [Ac-(D)-Phe$^{45}$,Pro$^{46}$ArgΨ[COCH$_2$]CH$_2$CH$_2$CO$^{47,48}$] Hirudin$^{45-65}$ (Hirutonin-3), and [Ac-(D)-Phe$^{45}$,Pro$^{46}$,ArgΨ [COCH$_2$]CH$_2$CH$_2$CH$_2$CO$^{47,48}$] Hirudin$^{45-65}$ (Hirutonin-4), DiMaio et al., J. Med. Chem., 35:3331–3341 (1992).

Growth Factor Inhibitors

Growth factors (GF) such as platelet derived growth factor (PDGF) are involved in vascular smooth muscle cell proliferation, which is considered the hallmark of restenosis and which occurs in 35 to 40% of patients within six months after coronary angioplasty. Califf et al., "Restenosis: The Clinical Issues," 363-94, Textbook of Interventional Cardiology, Topol. (ed.) (W.B. Saunders, Philadelphia, 1990).

GF antagonists such as somatostatin and its analogs have been used in animal and human clinical trials for the prevention of restenosis and are useful in the present invention. For example, the octapeptide somatostatin analog angiopeptin (D-β-Nal-Cys-Tyr-D-Trp-Lys-Val-Cys-Thr-NH$_2$, SEQ ID NO:7) and other somatostatin analogs have been shown to inhibit blood vessel blockage after angioplasty by inhibiting myotintimal proliferation in animal models as described in Ramwell et al., U.S. Pat. No. 5,147,856. Ramwell et al. also describes methods of synthesizing these analogs.

However, since the half-life of these peptides is only on the order of 3 to 5 minutes, delivery of adequate amounts to the diseased vessel is a major unsolved problem. Fusion of such a peptide with the A-chain of u-PA allows efficient anchoring of the peptide to the platelet membrane and provides a significant portion of the injected fusion drug with a long half-life. Moreover, since platelets aggregate at sites of vascular injury, the GF antagonists are effectively targeted to the site where smooth muscle cell proliferation occurs.

Examples of fusion drugs including hirudin or somatostatin are described below.

Chemically Linked Fusion Drugs

The two portions of the fusion drug, the A-chain portion and the drug or active portion thereof, can be individually synthesized or recombinantly produced by standard techniques and then chemically modified and linked by a covalent bond.

For example, a disulfide-linked hirudin-A-chain fusion protein is prepared by reacting an N-Succinimidyl 3-(2-pyridyldithio) propionate (SPDP, Pierce Chemical, Rockford, Ill.) derivative of hirudin with a portion of the A-chain of pro-UK as follows. 50 μM hirudin and 100 μM SPDP is added to 0.05 mM Tris-HCl buffer (pH 8.0), and incubated at 25° C. for 1 hour. Extra SPDP and other chemicals are removed by gel filtration or dialysis with 0.05 mM sodium acetate buffer (pH 4.5). 25mM DTT is added into the reaction mixture for 1 hour at pH 4.5 to thiolate the protein and prevent the reduction of disulfide bonds of hirudin. Any excess DTT and pyridine-2-thione can be removed by dialysis or gel filtration.

An equimolar amount of UK A-chain which contains a free -SH ($Cys^{148}$) is added together with 50 μM 2-pyridyle-disulfide activated hirudin in 0.05 μM sodium acetate buffer (pH 7.4) and incubated for 2 hours. The conjugated molecule is isolated by gel filtration, and antibody affinity columns using standard techniques.

All buffers should be degassed and treated with 0.0001 mM EDTA to avoid the oxidizing effect of extraneous metal ions. In addition, peak protein fractions can be pooled and analyzed for 2-pyridyldisulfide content (Carlsson et al., Biochem J., 173:723–737, 1978) and preferably show about 0.6 to 1.5 residues per hirudin molecule. The SPDP substitution level is kept intentionally low to limit loss of hirudin activity and to avoid formation of higher molecular weight aggregates. Further, basic reaction conditions, which lead to preferential modification of the amino-terminus of the protein, should be chosen.

Other thrombin antagonists and anti-GF proteins such as somatostatin and its analogs can be modified in a similar manner with SPDP as described above, or with succinimidyl 4-(N-maleimidomethyl)cyclohexane-1-carboxylate (SMCC, Sigma Chemical, St. Louis, Mo.), to add a single terminal thiol-reactive group.

The resulting fusion protein is purified by standard techniques, and its anti-thrombin activity can be measured with a standard assay for thrombin inhibition using the chromogenic substrate, S-2238 (H-D phenylalanyl-L-pipecolyl-L-arginine-p-nitroaniline dihydrochloride) (Chromogenix, Mödlndal, Sweden), as described in Abildgaard et al., Thromb. Res., 11:549–553 (1977). This assay can also be used to test the recombinant fusion drugs described below.

This assay can be carried out by adding 20 μl of thrombin solution (2.5 U/ml water) to 100 μl of a sample of hirudin or hirudin-A-chain fusion protein in assay buffer (20 mM sodium dihydrogen carbonate, 0.15 M NaCl, 0.1% BSA, pH 7.4) and incubating at room temperature for 10 min. Then 50 μl (0.833 mg/ml) of chromogenic substrate S-2238 is added. After exactly 5 min. of incubation, the reaction is stopped by addition of 50 μl 20% acetic acid, and the test results are read at 405 nm. Quantitation is obtained by comparing inhibition of thrombin activity in the test sample with that achieved by different known concentrations of unconjugated hirudin.

Recombinant Fusion Drugs

Drugs, e.g., hirudin, can be cloned to obtain cDNAs useful for the creation of recombinant fusion drugs. For example, hirudin cDNAs can be cloned using standard techniques as described in Harvey et al., P.N.A.S., USA, 83:1084–1088 (1986). Similarly, cDNAs encoding somatostatin and other GF antagonists can be cloned using standard techniques, e.g., as described in Canosi et al., U.S. Pat. No. 5,268,278. Synthetic genes encoding other antithrombin peptides or somatostatin analogs can be produced using standard techniques.

To obtain a nucleic acid that encodes a portion of the A-chain of u-PA, the cDNA encoding the full-length human pro-UK can be obtained as described in Verde et al., P.N.A.S., USA, 81:4727-31 (1984) or Holmes et al., "Cloning and expression of gene for pro-urokinase in Escherichia coli," Biotechnology, 3:923–929 (1985).

In general, the selected DNA, e.g., a portion of the A-chain, DNA encoding a cardiovascular drug, and an expression vector including promoter are ligated together to form a DNA construct. The DNA construct is transfected into, e.g., E. coli or preferably mammalian cells such as CHO cells, e.g., by electroporation or DEAE-dextran transfection, for expression of the recombinant fusion protein and selected for expression of the recombinant hybrid protein. If bacterial cells are used as hosts, the resulting fusion proteins must be fully denatured, e.g., with urea, diluted and isolated from the denaturant, and allowed to renature under appropriate conditions to form the active protein. If mammalian cells are used, the resulting fusion protein is generally secreted in the properly folded active form.

The fusion proteins are purified from the culture media by standard affinity chromatography purification. Preferably, a method is selected to ensure that both portions of the hybrid protein possess their correct function, e.g., first using a thrombin-Sepharose column to bind the hirudin portion, and then using an anti-A-chain antibody to bind the A-chain portion of the fusion protein.

For the general techniques of cloning the human cDNA gene for pro-UK, expressing pro-UK in mammalian cells, and purifying the pro-UK see, e.g., Gurewich et al., J. Clin. Invest., 82:1956-62 (1988).

A-Chain/Somatostatin Fusion Drug

Figure 7:
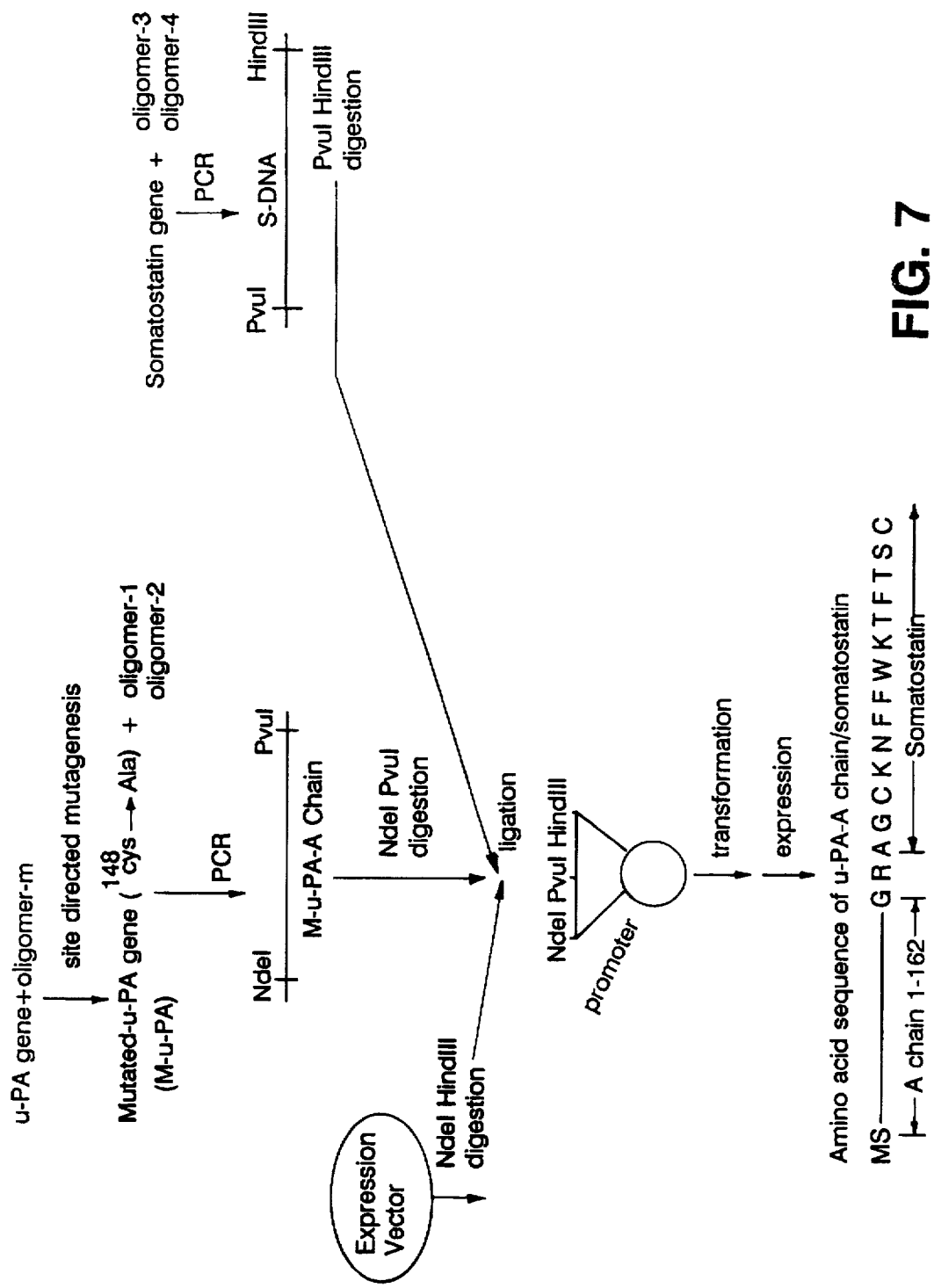
FIG. 7 is a flow chart of method steps to produce an A-chain/somatostatin fusion drug.

FIG. 7 shows a protocol to create an A-chain/somatostatin fusion drug. The uPA gene is used as template to obtain a portion of the A-chain. Oligomer-M (5'-TTAAAATTTCAGGCTGGCCAAAAA -3', SEQ ID NO:8) is used as a mutation primer for standard site directed mutagenesis to convert the $Cys^{148}$ codon of uPA into an Ala condon (at the location of the bold nucleotides in Oligomer-M) using standard techniques. This mutation avoids undesirable disulfide bonds that could result if this Cys residue remained.

This mutated uPA (m-uPA) gene is then used as a template with Oligomer-1 (5'-GGATTACATATGAGCAATGAACTTCAT-3', SEQ ID NO:9) and Oligomer-2 (3'-GCGAAATTCTAATAACCCGCTAGCAAGTGG -5', SEQ ID NO:10) as primers to amplify a portion of the A-chain DNA using standard polymerase chain reaction techniques. Oligomer-1 provides an NdeI restriction site at the bold nucleotides. Oligomer-2 provides a PvuI restriction site at the bold nucleotides. The resulting DNA is a mutated A-chain with NdeI and PvuI restriction sites as shown.

To obtain a useful portion of the somatostatin gene, the somatostatin gene is used as a template with oligomer-3 (5'-CTGCAGCGATCGGCTAACTCAAACCCGGCC -3', SEQ ID NO:11) and Oligomer-4 (3'- GAAAGTGTAGGA-CAATTCGAATAAT -5', SEQ ID NO:12) as primers to amplify DNA (S-DNA) using standard polymerase chain reaction techniques. Oligomer-3 provides a PvuI restriction site at the bold nucleotides. Oligomer-4 provides a HindIII restriction site at the bold nucleotides. The resulting S-DNA is a somatostatin DNA with PvuI and HindIII restriction sites as shown.

The m-uPA DNA is digested with NdeI and PvuI and purified by agarose gel electrophoresis. The S-DNA is digested with PvuI and HindIII, and purified by agarose gel electrophoresis. These two digested DNAs are then ligated together with an appropriate expression vector, e.g., pET29 (Novagen, Madison Wis.) digested with NdeI and HindIII to form a DNA construct that includes a promoter, the NdeI-PvuI portion of the A-chain, and the PvuI-HindIII portion of the somatostatin gene, as shown in FIG. 7, using standard techniques.

This DNA construct is then transformed and expressed in host cells, e.g., CHO cells, to form the fusion protein including amino acids 1 to 162 (amino acids S to G) of pro-UK and the amino acid sequence AGCKNFFWKT-FTSC (SEQ ID NO:13) of somatostatin, linked by an arginine (R) residue that corresponds to the PvuI restriction site.

A-Chain/Hirudin Fusion Drug

Figure 8:
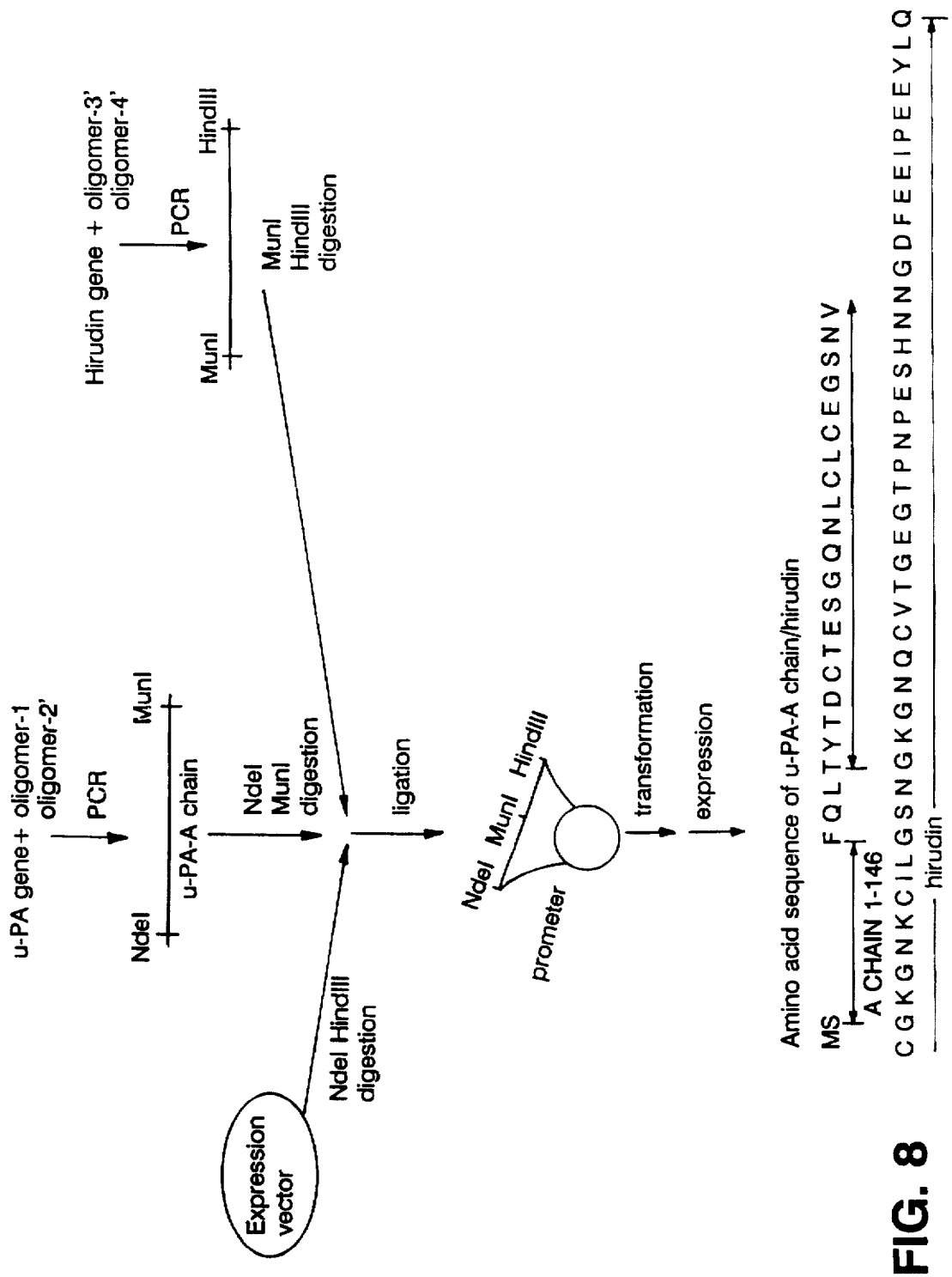
FIG. 8 is a flow chart of method steps to produce an A-chain/hirudin fusion drug.

FIG. 8 shows a protocol to create an A chain/hirudin fusion drug. The uPA gene is used as a template with Oligomer-1 (as above) and Oligomer-2' (3'-CTTCTTAATTTTAAAGTTAACACACCG -5', SEQ ID NO:14) as primers to amplify a portion of the A-chain DNA using standard polymerase chain reaction techniques. Oligomer-1 provides an NdeI restriction site at the bold nucleotides. Oligomer-2' provides a MunI restriction site at the bold nucleotides. The resulting DNA is a portion of the A-chain with NdeI and MunI restriction sites as shown.

To obtain a useful portion of the hirudin gene, the hirudin gene is used as a template with Oligomer-3' (5'-TCTCAACAATTGACTTACACGATTGT-3', SEQ ID NO:15) and Oligomer-4' (3'- TCTTATAAATGTTACTTC-GAACTTT -5', SEQ ID NO:16) as primers to amplify DNA (H-DNA) using standard polymerase chain reaction techniques. Oligomer-3' provides a MunI restriction site at the bold nucleotides. Oligomer-4' provides a HindIII restriction site at the bold nucleotides. The resulting H-DNA is a hirudin DNA with MunI and HindIII restriction sites as shown.

The A-chain DNA is digested with NdeI and MunI and purified by agarose gel electrophoresis. The H-DNA is digested with MunI and HindIII, and purified by agarose gel electrophoresis. These two digested DNAs are then ligated together with an appropriate expression vector digested with NdeI and HindIII to form a DNA construct that includes a promoter, the NdeI-MunI portion of the A-chain, and the MunI-HindIII portion of the hirudin gene, as shown in FIG. 8, using standard techniques.

This DNA construct is then transformed and expressed in host cells to form the fusion protein including amino acids 1 to 146 (amino acids S to F) of pro-UK and the amino acid sequence TYTDCTESGQNLCLCEGSN-VCGKGNKCILGSNG KGNQCVTGEGTPN-PESHNNGDFEEIPEEYLQ (SEQ ID NO:17 of hirudin (based on the sequence in Harvey et al., 1986) linked by glutamine (Q) and leucine (L) residues corresponding to the MunI restriction site.

Cleavage Sites

A mechanism that allows the drug portion to be released from the fusion drug after it is bound to the platelet outer membrane can be included in the fusion drug, since it is possible that a drug, e.g., a growth factor antagonist, may not be optimally effective when anchored to the platelet. Such a release mechanism can be created by using an amino acid sequence susceptible to cleavage by a local enzyme. In this case, thrombin or plasmin, which are concentrated on both the platelet surface and the vessel wall endothelium, are both good choices for use as this local enzyme. As a result of thrombin or plasmin-induced catalysis, local release of the peptide from the platelet surface would occur.

Figure 2:
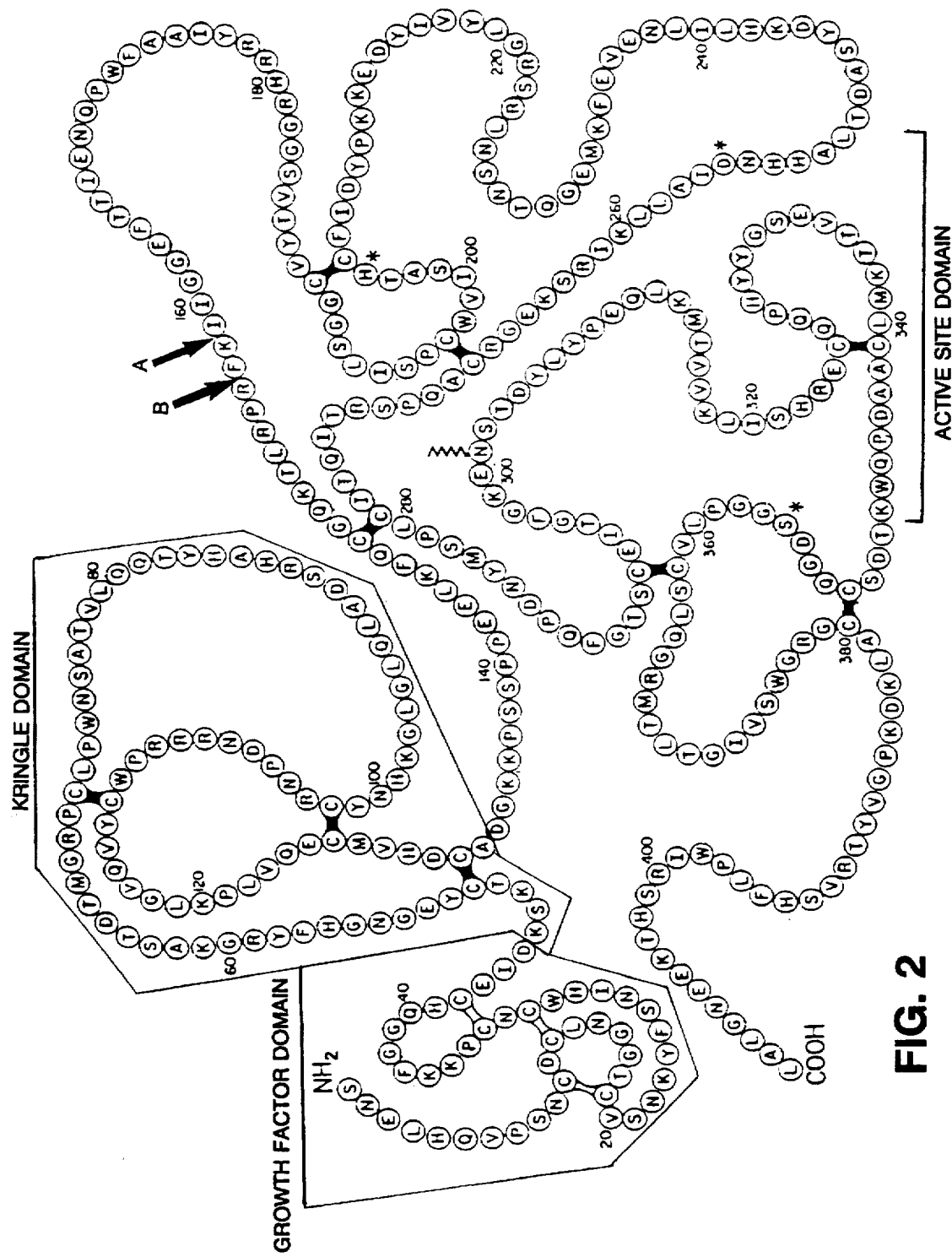
FIG. 2 is a schematic representation of the primary amino acid sequence of single chain pro-UK including the A-chain (SEQ ID NO:18).

To create this mechanism within the fusion drug, one can exploit the sensitive thrombin and plasmin cleavage sites in native pro-UK by extending the A-chain sequence beyond isoleucine[159] to about amino acid 165 or 170 to maintain an efficient substrate site, and mutating the now unpaired Cys[148] to another neutral amino acid, such as alanine or serine, e.g., using standard site-directed mutagenesis. These cleavage sites are shown in FIG. 2 at arrows A (plasmin cleavage site) and B (thrombin cleavage site).

Testing of Fusion Drugs

A number of animal models for testing the antithrombotic efficacy of drugs have been developed. For example, a canine model of coronary artery thrombosis with superimposed high grade stenosis for the investigation of rethrombosis after thrombolysis, as described in Yasuda et al., *J. Am. Coll. Cardiol.*, 13:1409–1414 (1989), can be used to test the fusion drugs of the invention. In addition, in vitro testing of platelet aggregation by thrombin can be used to test the effectiveness of the fusion drug.

In addition, since in most instances both components of the fusion drug have already been approved for human use, clinical testing will be readily available. This is especially important for testing the anti-growth factor fusion drugs, since good animal models for testing inhibitors of restenosis are not available for these drugs.

Use

The fusion drugs are useful to prevent blood clot formation and atherosclerotic stenosis of arteries. Thrombotic disorders characterized by excessive or unwanted clotting of blood underlie a number of serious health threats, such as unstable angina and myocardial infarction. Other conditions which may indicate the administration of the fusion drugs of the invention include but are not limited to pulmonary thromboembolism, cerebral embolism, peripheral arterial occlusion, peripheral emboli in limbs, coronary stent implantation, and PTCA. Stroke patients and patients recuperating from surgery, such as hip or back surgery, as well as patients confined to prolonged bed rest are at risk of developing undesirable thrombi, and thus, are candidates for therapeutic administration of the fusion drugs.

Administration

For the treatment of patients in such thrombogenic situations, the fusion drugs, e.g., proteins, are administered in a pharmaceutically acceptable carrier such as physiological saline, in the same way that SK or tPA are administered. The fusion drugs can be administered intraperitoneally, intramuscularly, subcutaneously, intravenously, or orally, although the preferred route of administration is intravenous with a dosage of approximately 0.001 to 0.5 mg/kg of body weight every 2 to 5 days. However, as is well known in the medical arts, dosages for any one patient depends upon many factors, including the patient's weight, body surface area, age, the particular compound to be administered, sex, time and route of administration, general health, and other drugs being administered concurrently.

The invention also includes an ex vivo method of therapy. This method of the invention is of particular benefit in situations in which the blood of a patient is removed for filtering, e.g., kidney dialysis, gas exchange procedures, or when the patient requires blood transfusions. For extracorporeal blood treatment, blood is removed from the individual using standard methods such as venous puncture. The fusion drug in a physiologically acceptable carrier is then be mixed with the blood, and subsequently returned to the individual using known methods such as intravenous drip.

In some cases, it can be useful to dissolve existing thrombotic occlusions in addition to preventing the formation of new clots. Administration of the fusion protein with either (1) a fibrinolytic agent such as SK, staphylokinase, or tPA, or (2) a second fusion drug containing a fibrin-binding domain linked to a fibrinolytic agent, would then be appropriate. The production of a thrombolytic agent containing a fibrin-specific antibody coupled to a fibrinolytic agent is described, e.g., in Haber et al., U.S. Pat. No. 5,116,613. These agents can be administered to a patient sequentially or simultaneously as described above.

Prophylactic Administration

Since the platelet membrane-bound fusion drug has a lifetime in the plasma equal to that of its platelet carrier, it will last 4 to 5 days on average, depending upon the age of the particular platelet by which it was incorporated. To keep the platelet compartment of the plasma maximally loaded with the fusion drug to achieve the long-term prophylactic effect according to the invention, the drug is preferably administered intravenously once every 1 to 3 days in a single bolus of about 0.001 to 0.5 mg/kg, and preferably 0.1 to 0.5 mg/kg. Longer intervals between injections, e.g., 5 to 10 days, may be used, but the effectiveness of such administration decreases as the interval between administrations increases.

Alternatively, the bolus may also be injected subcutaneously once every 1 to 3 days, and preferably daily, which provides the long-term prophylaxis according to the invention, and the added benefit of self-administration. Subcutaneous administration gives varying absorption rates, and can therefore be carried out with somewhat higher dosages.

Prevention of Reocclusion Following Thrombolytic Therapy

Reocclusion often occurs within hours after successful lysis of a thrombus with tPA, SK, or other thrombolytic agent, which substantially attenuates the therapeutic effect of these agents. To prevent such undesired reocclusion, a bolus of a fusion drug at the dosages described above is administered intravenously immediately, or within a few hours or a day, after the completion of thrombolytic therapy, and additional boluses at the same dosage are administered intravenously thereafter once daily throughout hospitalization, which is typically about 10 days. Thereafter, subcutaneous or intravenous injections of a similar dosage every 1 to 3 days are administered during the "risk period," which is about three to six months after thrombolysis.

The thrombolytic effect of tPA ends once infusion of the agent is completed, and the risk of reocclusion is the highest with tPA compared with other thrombolytic agents. Therefore, when tPA is used as the thrombolytic agent, a fusion drug should be administered to the patient immediately after the tPA infusion is finished.

When SK is used as the thrombolytic agent, major systemic effects arise, which have an anti-thrombotic effect for a few hours after the thrombolytic therapy is completed. Therefore, the fusion drug can be administered at any time within several hours after the completion of SK therapy.

When pro-UK is used as a thrombolytic agent, it is typically infused to lyse clots at a high dosage of, e.g., 80 mg/hour, and is associated with a low rate of reocclusion (1–5%) for at least the first 24 hours. Thus, a fusion drug should be administered, e.g., at 1 to 3 day intervals, starting 1 to 3 days after the initial administration of pro-UK is complete.

Prevention of Reocclusion Following PTCA

A principal limitation of PTCA for coronary artery stenoses is that about 30% of these lesions reocclude within three months. Although the pathophysiology of restenosis is not completely understood, it is generally believed to be mediated at least in part by platelets and the proliferation of smooth muscle cells. No effective therapy or prevention has been established.

According to the invention, this incidence of reocclusion is reduced by the administration of a bolus of a fusion drug injected intravenously immediately to within one day after completion of angioplasty, followed by subcutaneous injections of boluses once every 1 to 3 days for at least 3 months.

Treatment of Transient Arterial Insufficiency

Transient arterial insufficiency occurs when a diseased blood vessel is partially or completely occluded by the presence of fibrin and platelets at a site of damage in the vessel. Such an insufficiency in the brain results in so-called transient ischemic attacks, and in the heart results in unstable angina pectoris. Although such an occlusion may be temporary, it is typically associated with neurological symptoms in transient ischemic attacks and sharp pain in unstable angina. Transient ischemic attacks may also give rise to a stroke. Unstable angina pectoris, which is often due to "sputtering" coronary thrombosis, may herald an impending heart attack.

Thrombolytic therapy with available agents has not met with much success for these indications, because of their short duration of action, prothrombotic effects, and hemorrhagic complications with prolonged administration. In contrast, bolus intravenous or subcutaneous daily injections of a fusion drug during periods of ischemia and associated symptoms, and once every 1 to 3 days thereafter until the arterial insufficiency has stabilized, should be very effective to treat these diseases.

Prophylaxis of Cardiovascular Disease

Atherosclerosis and thrombosis in the arterial circulation are believed, in large part, to be platelet-mediated. According to the invention, intravenous or subcutaneous injections of an amount of a fusion drug, at regular intervals, e.g., every 3 to 10 days, should be a safe and effective prophylactic treatment for cardiovascular diseases including coronary disease such as angina, cerebral vascular disease such as transient ischemic attacks, and peripheral vascular disease such as peripheral arterial occlusions.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

I claim:

1. A fusion drug consisting of
   (a) a non-urokinase drug consisting of a peptide, protein, or polypeotide effective against a platelet-mediated thrombosis or stenosis;
   (b) a bvinding portion consisting of an isolated portion of at least amino acids 1 to 132 of the A-chain of a urokinase-type plasminogen activator (SEQ ID NO:18) that binds stably to an outer membrane of a platelet; and, optionally,
   (c) a linker region selected from the group of amino acid sequences consisting of amino acids 133 to 157, 133 to 158, 133 to 159, 133 to 160, 133 to 165, and 133 to 170, of a urokinase-type plasminogen activator (SEQ ID NO:18); wherein said binding portion is linked to the linker region, if present, or to the drug, and wherein said drug is linked to the carboxy terminal of said A-chain binding portion or to the linker region, if present.

2. A fusion drug of claim 1, wherein the sequence of amino acids of said binding portion is the sequence of amino acids 1 to 132 in SEQ ID NO:18.

3. A fusion drug of claim 1, wherein said linker region consists of amino acids 133 to 159 of the A-chain of pro-urokinase, which sequence includes the cleavate sites for thrombin and plasmin.

4. A fusion drug of claim 1, wherein said linker region consists of amino acids 133 to 157 of the A-chain of pro-urokinase, which sequence includes the cleavage site for thrombin.

5. A fusion drug of claim 1, wherein said drug is a thrombolytic agent.

6. A fusion drug of claim 1, wherein said drug is hirudin or a hirudin analog.

7. A fusion drug of claim 1, wherein said drug is a growth factor antagonist.

8. A fusion drug of claim 7, wherein said drug is somatostatin or a somatostatin analog.

9. A fusion drug of claim 1, wherein said drug is linked to said binding portion via a peptide bond.

10. A method of treatment of a platelet-mediated thrombosis or stenosis in a patient comprising administering to the patient an effective amount of a fusion drug of claim 1.

11. A method of adjunctive therapy to inhibit reocclusion in a patient after thrombolytic treatment, comprising administering to the patient a fusion drug of claim 1, said composition is administered after the completion of the thrombolytic treatment and once every 1 to 10 days thereafter for the period of risk of reocclusion.

\* \* \* \* \*

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
        ( A ) LENGTH: 1233
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
AGC  AAT  GAA  CTT  CAT  CAA  GTT  CCA  TCG  AAC  TGT  GAC  TGT  CTA  AAT  GGA        48
Ser  Asn  Glu  Leu  His  Gln  Val  Pro  Ser  Asn  Cys  Asp  Cys  Leu  Asn  Gly
                    5                        10                       15

GGA  ACA  TGT  CTG  TCC  AAC  AAG  TAC  TTC  TCC  AAC  ATT  CAC  TGG  TGC  AAC        96
Gly  Thr  Cys  Val  Ser  Asn  Lys  Tyr  Phe  Ser  Asn  Ile  His  Trp  Cys  Asn
               20                       25                       30

TGA  CCA  AAG  AAA  TTC  GGA  GGG  CAG  CAC  TGT  GAA  ATA  GAT  AAG  TCA  AAA       144
Cys  Pro  Lys  Lys  Phe  Gly  Gly  Gln  His  Cys  Glu  Ile  Asp  Lys  Ser  Lys
          35                            40                       45

ACC  TGC  TAT  GAG  GGG  AAA  GGT  CAC  TTT  TAC  CGA  GGA  AAG  GCC  AGC  ACT       192
Thr  Cys  Tyr  Glu  Gly  Asn  Gly  His  Phe  Tyr  Arg  Gly  Lys  Ala  Ser  Thr
     50                       55                            60

GAC  ACC  ATG  GGC  CGG  CCC  TGC  CTG  CCC  TGG  AAC  TCT  GCC  ACT  GTC  CTT       240
Asp  Thr  Met  Gly  Arg  Pro  Cys  Leu  Pro  Trp  Asn  Ser  Ala  Thr  Val  Leu
65                       70                       75                        80

CAG  CAA  ACG  TAC  CAT  GCC  CAC  AGA  TCT  GAT  GCT  CTT  CAG  CTG  GGC  CTG       288
Gln  Gln  Thr  Tyr  His  Ala  His  Arg  Ser  Asp  Ala  Leu  Gln  Leu  Gly  Leu
                    85                       90                            95

GGG  AAA  CAT  AAT  TAC  TGC  AGG  AAC  CCA  GAC  AAC  CGG  AGG  CGA  CCC  TGG       336
Gly  Lys  His  Asn  Tyr  Cys  Arg  Asn  Pro  Asp  Asn  Arg  Arg  Arg  Pro  Trp
               100                      105                     110

TGC  TAT  GTG  CAG  GTG  GGC  CTA  AAG  CCG  CTT  GTC  CAA  GAG  TGC  ATG  GTG       384
Cys  Tyr  Val  Gln  Val  Gly  Leu  Lys  Pro  Leu  Val  Gln  Glu  Cys  Met  Val
          115                           120                     125

CAT  GAC  TGC  GCA  GAT  GGA  AAA  AAG  CCC  TCC  TCT  CCT  CCA  GAA  GAA  TTA       432
His  Asp  Cys  Ala  Asp  Gly  Lys  Lys  Pro  Ser  Ser  Pro  Pro  Glu  Glu  Leu
     130                      135                      140

AAA  TTT  CAG  TGT  GGC  CAA  AAG  ACT  CTG  AGG  CCC  CGC  TTT  AAG  ATT  ATT       480
Lys  Phe  Gln  Cys  Gly  Gln  Lys  Thr  Leu  Arg  Pro  Arg  Phe  Lys  Ile  Ile
145                      150                      155                      160

GGG  GGA  GAA  TTC  ACC  ACC  ATC  GAG  AAC  CAG  CCC  TGG  TTT  GCG  GCC  ATC       528
Gly  Gly  Glu  Phe  Thr  Thr  Ile  Glu  Asn  Gln  Pro  Trp  Phe  Ala  Ala  Ile
                    165                      170                     175

TAC  AGG  AGG  CAC  CGG  GGG  GGC  TCT  GTC  ACC  TAC  GTG  TGT  GGA  GGC  AGC       576
Tyr  Arg  Arg  His  Arg  Gly  Gly  Ser  Val  Thr  Tyr  Val  Cys  Gly  Gly  Ser
               180                      185                      190

CTC  ATC  AGC  CCT  TGC  TGG  GTG  ATC  AGC  GCC  ACA  CAC  TGC  TTC  ATT  GAT       624
Leu  Ile  Ser  Pro  Cys  Trp  Val  Ile  Ser  Ala  Thr  His  Cys  Phe  Ile  Asp
          195                      200                      205

TAC  CCA  AAG  AAG  GAG  GAC  TAC  ATC  GTC  TAC  CTG  GGT  CGC  TCA  AGG  CTT       672
Tyr  Pro  Lys  Lys  Glu  Asp  Tyr  Ile  Val  Tyr  Leu  Gly  Arg  Ser  Arg  Leu
     210                      215                      220

AAC  TCC  AAC  ACG  CAA  GGG  GAG  ATG  AAG  TTT  GAG  GTG  GAA  AAC  CTC  ATC       720
Asn  Ser  Asn  Thr  Gln  Gly  Glu  Met  Lys  Phe  Glu  Val  Glu  Asn  Leu  Ile
225                      230                      235                      240

CTA  CAC  AAG  GAC  TAC  AGC  GCT  GAC  ACG  CTT  GCT  CAC  CAC  AAC  GAC  ATT       768
Leu  His  Lys  Asp  Tyr  Ser  Ala  Asp  Thr  Leu  Ala  His  His  Asn  Asp  Ile
```

|  |  |  |  |  |  |  |  |  |  |  |  |  |  |  |  |
|---|---|---|---|---|---|---|---|---|---|---|---|---|---|---|---|
|  |  |  | 245 |  |  |  | 250 |  |  |  | 255 |  |  |  |  |
| GCC | TTG | CTG | AAG | ATC | CGT | TCC | AAG | GAG | GGC | AGG | TGT | GCG | CAG | CCA | TCC | 816 |
| Ala | Leu | Leu | Lys 260 | Ile | Arg | Ser | Lys | Glu 265 | Gly | Arg | Cys | Ala | Gln 270 | Pro | Ser |  |
| CGG | ACT | ATA | CAG | ACC | ATC | TGC | CTG | CCC | TCG | ATG | TAT | AAC | GAT | CCC | CAG | 864 |
| Arg | Thr | Ile 275 | Gln | Thr | Ile | Cys | Leu 280 | Pro | Ser | Met | Tyr | Asn 285 | Asp | Pro | Gln |  |
| TTT | GGC | ACA | AGC | TGT | GAG | ATC | ACT | GGC | TTT | GGA | AAA | GAG | AAT | TCT | ACC | 912 |
| Phe | Gly | Thr 290 | Ser | Cys | Glu | Ile 295 | Thr | Gly | Phe | Gly | Lys | Glu 300 | Asn | Ser | Thr |  |
| GAC | TAT | CTC | TAT | CCG | GAG | CAG | CTG | AAG | ATG | ACT | GTT | GTG | AAG | CTG | ATT | 960 |
| Asp 305 | Tyr | Leu | Tyr | Pro | Glu 310 | Gln | Leu | Lys | Met | Thr 315 | Val | Val | Lys | Leu | Ile 320 |  |
| TCC | CAC | CGG | GAG | TGT | CAG | CAG | CCC | CAC | TAC | TAC | GGC | TCT | GAA | GTC | ACC | 1008 |
| Ser | His | Arg | Glu | Cys 325 | Gln | Gln | Pro | His | Tyr 330 | Tyr | Gly | Ser | Glu | Val 335 | Thr |  |
| ACC | AAA | ATG | CTG | TGT | GCT | GCT | GAC | CCA | CAG | TGG | AAA | ACA | GAT | TCC | TGC | 1056 |
| Thr | Lys | Met | Leu 340 | Cys | Ala | Ala | Asp | Pro 345 | Gln | Trp | Lys | Thr | Asp 350 | Ser | Cys |  |
| CAG | GGA | GAC | TCA | GGG | GGA | CCC | CTC | GTC | TGT | TCC | CTC | CAA | GGC | CGC | ATG | 1104 |
| Gln | Gly | Asp 355 | Ser | Gly | Gly | Pro | Leu 360 | Val | Cys | Ser | Leu | Gln 365 | Gly | Arg | Met |  |
| ACT | TTG | ACT | GGA | ATT | GTG | AGC | TGG | GGC | CGT | GGA | TGT | GCC | CTG | AAG | GAC | 1152 |
| Thr | Leu 370 | Thr | Gly | Ile | Val | Ser 375 | Trp | Gly | Arg | Gly | Cys 380 | Ala | Leu | Lys | Asp |  |
| AAG | CCA | GGC | GTC | TAC | ACG | AGA | GTC | TCA | CAC | TTC | TTA | CCC | TGG | ATC | CGC | 1200 |
| Lys 385 | Pro | Gly | Val | Tyr | Thr 390 | Arg | Val | Ser | His | Phe 395 | Leu | Pro | Trp | Ile | Arg 400 |  |
| AGT | CAC | AAC | AAG | GAA | GAG | AAT | GGC | CTG | GCC | CTC |  |  |  |  |  | 1233 |
| Ser | His | Thr | Lys | Glu 405 | Glu | Asn | Gly | Leu | Ala 410 | Leu |  |  |  |  |  |  |

( 2 ) INFORMATION FOR SEQ ID NO: 2:

( i ) SEQUENCE CHARACTERISTICS:
    ( A ) LENGTH: 66
    ( B ) TYPE: amino acid
    ( C ) STRANDEDNESS: single
    ( D ) TOPOLOGY: linear ( x i ) SEQUENCE DESCRIPTION: SEQ ID NO: 2:

| Ile 1 | Thr | Tyr | Thr | Asp 5 | Cys | Thr | Glu | Ser | Gly 10 | Gln | Asn | Leu | Cys | Leu 15 | Cys |
|---|---|---|---|---|---|---|---|---|---|---|---|---|---|---|---|
| Glu | Gly | Ser | Asn 20 | Val | Cys | Gly | Lys | Gly 25 | Asn | Lys | Cys | Ile | Leu 30 | Gly | Ser |
| Gln | Gly | Lys 35 | Asp | Asn | Gln | Cys | Val 40 | Thr | Gly | Glu | Gly | Thr 45 | Pro | Lys | Pro |
| Gln | Ser 50 | His | Asn | Gln | Gly | Asp 55 | Phe | Glu | Pro | Ile | Pro 60 | Glu | Asp | Ala | Tyr |
| Asp 65 | Glu |  |  |  |  |  |  |  |  |  |  |  |  |  |  |

( 2 ) INFORMATION FOR SEQ ID NO: 3:

( i ) SEQUENCE CHARACTERISTICS:
    ( A ) LENGTH: 12
    ( B ) TYPE: amino acid
    ( C ) STRANDEDNESS: single
    ( D ) TOPOLOGY: linear ( i x ) FEATURE:
    ( D ) OTHER INFORMATION: Xaa is COOH, Leu or Leu-Gln ( x i ) SEQUENCE DESCRIPTION: SEQ ID NO: 3:

Asn Gly Asp Phe Glu Glu Ile Pro Glu Glu Tyr Xaa
 1                   5                      10

( 2 ) INFORMATION FOR SEQ ID NO: 4:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i x ) FEATURE:
        ( D ) OTHER INFORMATION: Xaa is COOH, Leu, or Leu-Gln ( x i ) SEQUENCE DESCRIPTION: SEQ ID NO: 4:

Phe Glu Glu Ile Pro Glu Glu Tyr Xaa
 1                   5

( 2 ) INFORMATION FOR SEQ ID NO: 5:

( i ) SEQUENCE CHARACTERISTICS:
        ( A ) LENGTH: 12
        ( B ) TYPE: amino acid
        ( C ) STRANDEDNESS: single
        ( D ) TOPOLOGY: linear ( x i ) SEQUENCE DESCRIPTION: SEQ ID NO: 5:

Asn Gly Asp Phe Glu Glu Ile Pro Glu Glu Tyr Leu
 1                   5                      10

( 2 ) INFORMATION FOR SEQ ID NO: 6:

( i ) SEQUENCE CHARACTERISTICS:
        ( A ) LENGTH: 20
        ( B ) TYPE: amino acid
        ( C ) STRANDEDNESS: single
        ( D ) TOPOLOGY: linear ( x i ) SEQUENCE DESCRIPTION: SEQ ID NO: 6:

Phe Pro Arg Pro Gly Gly Gly Gly Asn Gly Asp Phe Glu Glu Ile Pro
 1                   5                      10                      15

Glu Glu Tyr Leu
              20

( 2 ) INFORMATION FOR SEQ ID NO: 7:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa is D- - Naphthylalanine ( x i ) SEQUENCE DESCRIPTION: SEQ ID NO: 7:

Xaa Cys Tyr Trp Lys Val Cys Thr
 1                   5

( 2 ) INFORMATION FOR SEQ ID NO: 8:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO: 8:

TTAAAATTTC AGGCTGGCCA AAAA                                                          24

( 2 ) INFORMATION FOR SEQ ID NO: 9:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GGATTACATA TGAGCAATGA ACTTCAT                                                       27

( 2 ) INFORMATION FOR SEQ ID NO: 10:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GCGAAATTCT AATAACCCGC TAGCAAGTGG                                                    30

( 2 ) INFORMATION FOR SEQ ID NO: 11:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CTGCAGCGAT CGGCTAACTC AAACCCGGCC                                                    30

( 2 ) INFORMATION FOR SEQ ID NO: 12:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GAAAGTGTAG GACAATTCGA ATAAT                                                         25

( 2 ) INFORMATION FOR SEQ ID NO: 13:

( i ) SEQUENCE CHARACTERISTICS:
        ( A ) LENGTH: 14
        ( B ) TYPE: amino acid
        ( C ) STRANDEDNESS: single
        ( D ) TOPOLOGY: linear ( x i ) SEQUENCE DESCRIPTION: SEQ ID NO: 13:

Ala Gly Cys Lys Asn Phe Phe Trp Lys Thr Phe Thr Ser Cys
1               5                   10

( 2 ) INFORMATION FOR SEQ ID NO: 14:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 14:

```
CTTCTTAATT TTAAAGTTAA CACACCG                                                              27
```

( 2 ) INFORMATION FOR SEQ ID NO: 15:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO: 15:

```
TCTCAACAAT TGACTTACAC GATTGT                                                               26
```

( 2 ) INFORMATION FOR SEQ ID NO: 16:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 16:

```
TCTTATAAAT GTTACTTCGA ACTTT                                                                25
```

( 2 ) INFORMATION FOR SEQ ID NO: 17:

( i ) SEQUENCE CHARACTERISTICS:
        ( A ) LENGTH: 64
        ( B ) TYPE: amino acid
        ( C ) STRANDEDNESS: single
        ( D ) TOPOLOGY: linear ( x i ) SEQUENCE DESCRIPTION: SEQ ID NO: 17:

```
Thr Tyr Thr Asp Cys Thr Glu Ser Gly Gln Asn Leu Cys Leu Cys Glu
 1               5                  10                  15
Gly Ser Asn Val Cys Gly Lys Gly Asn Lys Cys Ile Leu Gly Ser Asn
                20                  25                  30
Gly Lys Gly Asn Gln Cys Val Thr Gly Glu Gly Thr Pro Asn Pro Glu
                35              40                  45
Ser His Asn Asn Gly Asp Phe Glu Glu Ile Pro Glu Glu Tyr Leu Gln
            50              55                  60
```

( 2 ) INFORMATION FOR SEQ ID NO: 18:

( i ) SEQUENCE CHARACTERISTICS:
        ( A ) LENGTH: 411
        ( B ) TYPE: amino acid
        ( C ) STRANDEDNESS: single
        ( D ) TOPOLOGY: linear ( x i ) SEQUENCE DESCRIPTION: SEQ ID NO: 18:

```
Ser Asn Glu Leu His Gln Val Pro Ser Asn Cys Asp Cys Leu Asn Gly
 1               5                  10                  15
Gly Thr Cys Val Ser Asn Lys Tyr Phe Ser Asn Ile His Trp Cys Asn
                20                  25                  30
Cys Pro Lys Lys Phe Gly Gly Gln His Cys Glu Ile Asp Lys Ser Lys
                35              40                  45
Thr Cys Tyr Glu Gly Asn Gly His Phe Tyr Arg Gly Lys Ala Ser Thr
            50              55                  60
Asp Thr Met Gly Arg Pro Cys Leu Pro Trp Asn Ser Ala Thr Val Leu
65                  70                  75                  80
Gln Gln Thr Tyr His Ala His Arg Ser Asp Ala Leu Gln Leu Gly Leu
                85                  90                  95
```

```
Gly  Lys  His  Asn  Tyr  Cys  Arg  Asn  Pro  Asp  Asn  Arg  Arg  Arg  Pro  Trp
               100                      105                     110

Cys  Tyr  Val  Gln  Val  Gly  Leu  Lys  Pro  Leu  Val  Gln  Glu  Cys  Met  Val
               115                      120                     125

His  Asp  Cys  Ala  Asp  Gly  Lys  Lys  Pro  Ser  Ser  Pro  Pro  Glu  Glu  Leu
     130                      135                     140

Lys  Phe  Gln  Cys  Gly  Gln  Lys  Thr  Leu  Arg  Pro  Arg  Phe  Lys  Ile  Ile
145                           150                     155                     160

Gly  Gly  Glu  Phe  Thr  Thr  Ile  Glu  Asn  Gln  Pro  Trp  Phe  Ala  Ala  Ile
                    165                      170                          175

Tyr  Arg  Arg  His  Arg  Gly  Gly  Ser  Val  Thr  Tyr  Val  Cys  Gly  Gly  Ser
               180                      185                          190

Leu  Ile  Ser  Pro  Cys  Trp  Val  Ile  Ser  Ala  Thr  His  Cys  Phe  Ile  Asp
          195                      200                     205

Tyr  Pro  Lys  Lys  Glu  Asp  Tyr  Ile  Val  Tyr  Leu  Gly  Arg  Ser  Arg  Leu
     210                      215                     220

Asn  Ser  Asn  Thr  Gln  Gly  Glu  Met  Lys  Phe  Glu  Val  Glu  Asn  Leu  Ile
225                           230                     235                     240

Leu  His  Lys  Asp  Tyr  Ser  Ala  Asp  Thr  Leu  Ala  His  His  Asn  Asp  Ile
                    245                      250                          255

Ala  Leu  Leu  Lys  Ile  Arg  Ser  Lys  Glu  Gly  Arg  Cys  Ala  Gln  Pro  Ser
               260                      265                     270

Arg  Thr  Ile  Gln  Thr  Ile  Cys  Leu  Pro  Ser  Met  Tyr  Asn  Asp  Pro  Gln
          275                      280                     285

Phe  Gly  Thr  Ser  Cys  Glu  Ile  Thr  Gly  Phe  Gly  Lys  Glu  Asn  Ser  Thr
     290                      295                     300

Asp  Tyr  Leu  Tyr  Pro  Glu  Gln  Leu  Lys  Met  Thr  Val  Val  Lys  Leu  Ile
305                      310                     315                          320

Ser  His  Arg  Glu  Cys  Gln  Gln  Pro  His  Tyr  Tyr  Gly  Ser  Glu  Val  Thr
                    325                      330                          335

Thr  Lys  Met  Leu  Cys  Ala  Ala  Asp  Pro  Gln  Trp  Lys  Thr  Asp  Ser  Cys
               340                      345                     350

Gln  Gly  Asp  Ser  Gly  Gly  Pro  Leu  Val  Cys  Ser  Leu  Gln  Gly  Arg  Met
          355                      360                     365

Thr  Leu  Thr  Gly  Ile  Val  Ser  Trp  Gly  Arg  Gly  Cys  Ala  Leu  Lys  Asp
     370                      375                     380

Lys  Pro  Gly  Val  Tyr  Thr  Arg  Val  Ser  His  Phe  Leu  Pro  Trp  Ile  Arg
385                      390                     395                          400

Ser  His  Thr  Lys  Glu  Glu  Asn  Gly  Leu  Ala  Leu
                    405                      410
```